(12) United States Patent
Gangarosa, Sr.

(10) Patent No.: US 6,391,284 B1
(45) Date of Patent: May 21, 2002

(54) NONALCOHOLIC PHARMACEUTICAL PREPARATIONS FROM FORMULATIONS INCLUDING ALCOHOL AND PROCESS FOR THE PREPARATION THEREOF

(76) Inventor: Louis P. Gangarosa, Sr., 3304 Somerset Pl., Augusta, GA (US) 30909-3136

( * ) Notice: Subject to any disclaimer, the term of this patent is extended or adjusted under 35 U.S.C. 154(b) by 0 days.

(21) Appl. No.: 09/871,466

(22) Filed: May 31, 2001

(51) Int. Cl.⁷ .................................................. A61K 7/16
(52) U.S. Cl. ....................................................... 424/49
(58) Field of Search ........................................... 424/49

(56) References Cited

U.S. PATENT DOCUMENTS

| | | |
|---|---|---|
| 4,634,588 A | 1/1987 | Moroe |
| 4,919,918 A | 4/1990 | Cole et al. |
| 4,971,785 A | 11/1990 | Wilson et al. |
| 4,992,259 A | 2/1991 | Schiraldi et al. |
| 5,145,664 A | 9/1992 | Thompson |
| 5,283,056 A | 2/1994 | Chung et al. |
| 5,284,648 A | 2/1994 | White et al. |
| 5,292,527 A | 3/1994 | Konopa |
| 5,407,664 A | 4/1995 | Konopa |
| 5,560,906 A | 10/1996 | Scodari et al. |
| 5,688,491 A | 11/1997 | Shahidi |
| 5,817,295 A | 10/1998 | Chaudhari et al. |
| 5,891,422 A | 4/1999 | Pan et al. |

*Primary Examiner*—Raymond Henley, III
(74) *Attorney, Agent, or Firm*—Welsh & Katz, Ltd.

(57) ABSTRACT

A process of removing alcohol(s) from an alcoholic aqueous pharmaceutical preparation provides for the removal of alcohol(s) from alcoholic aqueous pharmaceutical preparation formulated in the presence of alcohol by utilizing a distillation step. The distillation process results in a chemically and physically stable, substantially nonalcoholic pharmaceutical preparation or a reduced alcoholic preparation. Furthermore, the resulting substantial nonalcoholic pharmaceutical preparations or reduced alcoholic preparation prepared by the distillation process is useful for preparing, inter alia, products which may vary from oral hygiene products such as mouthwashes, toothpaste and oral rinses, to skin care products.

39 Claims, No Drawings

NONALCOHOLIC PHARMACEUTICAL PREPARATIONS FROM FORMULATIONS INCLUDING ALCOHOL AND PROCESS FOR THE PREPARATION THEREOF

FIELD OF THE INVENTION

This invention relates generally to a process based on the removal of alcohol from alcoholic/aqueous pharmaceutical preparations, and more particularly to a nonalcoholic pharmaceutical composition, formulated in the presence of alcohol, obtained by performing the process.

BACKGROUND OF THE INVENTION

Pharmaceutical preparations typically need a vehicle which allows for the dissolution of components necessary to produce the final product. The vehicle is commonly ethyl alcohol, which is used to provide a fully dissolved and chemically and physically stable pharmaceutical composition. Particularly for example, in mouthwashes, oral rinses, and other pharmaceutical preparation used in maintaining oral hygiene, the use of alcohol is believed to be essential for solubilization of the components of the formulation. Without the ability to completely dissolve active compounds within a preparation and have these compounds remain both chemically and physically stable in the preparation, the resulting pharmaceutical composition could be therapeutically ineffective, unstable and unclear and result in inactivity against tooth decay, plaque, gum disease and oral ulcers.

Most conventional pharmaceutical compositions including mouthwashes and oral rinses contain a significantly high level of ethyl alcohol in their compositions. Typically, the level of ethyl alcohol ranges from 10% to 30% by volume, based on the total mouthwash volume. Generally, alcohol is used in pharmaceutical formulations not only for its disinfecting function, but also to assist in the dissolution of other compounds in the formulation, and to maintain a role as an effective preservative during storage.

Understandably, however the uses of alcohol in consumer health products has become undesirable, and imposes a number of inherent limitations and detrimental side effects upon use. Notwithstanding, the potential medical and health problems of which alcohol's inclusion in a wide variety of pharmaceutical compositions and orally ingested products imposes, the presence of alcohol also presents potential social implications for some users. Typically, the ingestion of alcohol even in small doses is likely to cause drowsiness, and should be avoided when operating heavy machinery and automobiles. Additionally, alcohol and its abuse is a recognized major social problem. Abuse of alcohol in all its forms is considered an illness, and contact with non-beverage alcohol can trigger setbacks in recovering alcoholics. Therefore, a substantially nonalcoholic aqueous pharmaceutical preparation used in maintaining oral hygiene is desirable, inter alia, for the safety of those individuals who cannot or should not use an oral aqueous pharmaceutical composition containing alcohol.

Furthermore, ethyl alcohol containing pharmaceutical compositions including oral rinses are generally not recommended for use by children. Many parents are concerned about the alcohol content, while many children reject the alcohol bite and astringency characteristics of such products. Moreover, the use of alcohol in many pharmaceutical compositions including orally ingested products results in gingival, periodontal and soft tissue irritation. At such time, alcoholic rinses cause even greater pain and are often replaced by rinsing with water, without receiving the benefits of the pharmaceutically active components. Even the substitution of ethyl alcohol with other solubilizing alcohols such as methanol or isopropyl alcohol in pharmaceutical preparations that have some potential for ingestion, have been found to be even more objectionable because they have local and systemic toxicities.

Over the years different strategies have been employed to achieve a pharmaceutical composition that effectively maintains its chemical and physical stability, yet does not contain alcohol. In cases of oral hygiene compositions, the art has been unable to successfully produce an oral composition by a simple and economical process that results in an alcohol free preparation that still effectively eliminates bacteria. Some antimicrobial compositions contain a reduced amount of alcohol in the presence of flavoring oils and surfactants, while others have incorporated flavoring oils and antibacterial agents in a dry formulation which is dissolved in water just prior to use, requiring preparation by the user.

In summary, several approaches have been explored to achieve a nonalcoholic composition, however none have been able to achieve an improved process that successfully removes alcohol from the composition while still maintaining stability and effectiveness. The art, therefore, lacks a stable and clear substantially nonalcoholic, aqueous pharmaceutical composition, which is physically and chemically effective. It is therefore an object of the present invention to provide a process which can achieve an effective, stable and clear substantially nonalcoholic aqueous pharmaceutical composition. A further objective of the present invention is to provide a method for solubilizing substances not normally soluble in water to form an aqueous substantially nonalcoholic preparation.

SUMMARY OF THE INVENTION

The present invention is directed to a process of converting a alcoholic/aqueous pharmaceutical preparations into aqueous nonalcoholic or reduced alcoholic solutions by distillation to remove alcohol(s). Particular, the invention comprises the introduction of a distillation method, which produces nonalcoholic or reduced alcoholic pharmaceutical preparations, formulated in the presence of alcohol. More particularly this invention relates to the removal of alcohol(s) from a pharmaceutical preparation through the process of distillation resulting in the production of an effective mouthwash, oral rinse and other pharmaceutical preparation used in maintaining oral hygiene. Further, the process can be used to prepare aqueous, substantially non-alcoholic preparation of active ingredients that normally are soluble in alcohols and do not dissolve in water.

DETAILED DESCRIPTION OF A PREFERRED EMBODIMENT

The present invention provides a process of removing alcohol from a pharmaceutical preparation resulting in a non-alcoholic composition or reduced alcoholic composition that is effective and physically and chemically stable.

The process of heating a liquid until its more volatile constituents pass into vapor phase and in turn separate from a mixture of several components is known as distillation. Distillation has been utilized in a number of chemical applications for the use of separating components within a mature. In contrast, however, the present invention uses the process of disillusion to remove alcohol(s) from alcoholic/aqueous pharmaceutical preparations and thus provide a substantially nonalcoholic aqueous pharmaceutical preparation formulated in the presence of alcohol, which is chemically and physically stable in the absence of alcohol. In other words, the distillation process of the subject invention is used to formulate a substantially nonalcoholic/aqueous pharmaceutical that was, formulated in the presence of alcohol.

A pharmaceutical preparation is dissolved and formulated by conventional means with the use of alcohol(s). The alcohol(s) used in the present invention may have various forms. Typically, the alcohol(s) used in the invention are alcohol(s) having a boiling point of less than water (100° C.), and preferably an alcohol having a boiling point less than 80° C. Methanol (boiling point 65° C.) and/or ethanol (boiling point 78.5° C.) are alcohols particularly useful in the present invention because their boiling points are lower than water (boiling point 100° C.). Alcohol(s) which may be used in connection with the subject invention may be alcohol(s) having 1 or more carbon atoms. Preferably, alcohol having 1 to 3 carbons and more preferably alcohol having 1 to 2 carbon atoms are used in connection with the practice of the present invention. As such, the most preferred alcohol(s) are ethanol and/or methanol. Furthermore, the typical levels of alcohol used in the present invention range from about 2.5% to about 30% by volume, preferably at a range of from about 5% to about 25% by volume and more preferably from a range of approximately 10% to approximately 20% by volume, based on the total composition volume before distillation.

The aqueous-alcoholic pharmaceutical formulation is then distilled at a temperature within the range of about 50° to less than 100° C., preferably approximately at a temperature within the range of from about 70° to about 90° C., and more preferably at a temperature within the range of approximately 75° 80° C. The distillation process is continued at a temperature within the specified range until all or almost all of the liquid volume equivalent to the alcohol has been removed.

One embodiment of the subject invention uses a stabilizing solution, which is clear and stable comprised of a combination of water, ethyl alcohol, a surface active agent (surfactant), either anionic or non-ionic, glycerin and polyhydric alcohol sorbitol. The stabilizing solution is used for dissolution and formulation of other pharmaceutical preparations in the formulation to be distilled in accordance with the invention to obtain a nonalcoholic product for mouth and skin use. Typically, in the process the stabilizing solution is used to dissolve a pharmaceutical compound thereby, forming an aqueous-alcoholic pharmaceutical formulation which is distilled at a temperature within the range of from about 50° to less than 100° C., preferably approximately at a temperature within the range of from about 70°–90° C., and more preferably at a temperature of approximately 75°–80° C. The distillation process is continued at a temperature within the specified range until all or almost all of the liquid volume equivalent to the alcohol has been removed.

The preferred embodiment of the invention utilizes the combination of a surface active agent (surfactant), either anionic or non-ionic, preferably a non-ionic surfactant (e.g. Pluronic gel, in powder form, marketed by BASF Corp. Mount Olive, N.J.) at a range of from about 0.002% to about 0.15% (gm/100 ml), and preferably from about 0.005 % to about 0.75% (gm/ml) in cooperation with glycerin at a range of from about 1% to about 20% (ml/100 ml) and the polyhydric alcohol sorbitol, at a range of from about 2% to about 20% (ml/100 ml), which forms a preparation used in combination with alcohol to dissolve pharmaceutical compounds, in the process of the invention. Although the inventor does not wish to be bound by any particular theory of the invention it is believed that this combination maintains the solubility of other ingredients after the alcohol is removed. As such, a pharmaceutical compound is dissolved in the combination of alcohol, surface agent, glycerin and the polyhydric alcohol sorbitol, forming an aqueous-alcoholic pharmaceutical formulation which is than distilled by the process of the invention detailed above until approximately almost all of the liquid equivalent to the alcohol volume has been removed.

A further embodiment of the subject invention uses a compound known as OOralief®. Oralief®, is marketed by HTC Corporation, Augusta, Georgia. The Oralief® compound contains all of the required compounds as described above, plus some additional active chemicals and pharmaceutical ingredients, such as phenol, within a range of from about 0.10%–1.0%, flavorings, glycerin, and surfactants, preferably a non-ionic surfactant (e.g., Pluronic F 127®, marketed by BASF Corp. Mount Olive, N.J.).

This preferred embodiment of the pharmaceutical preparation of the present invention utilizes Oralief® to produce a new nonalcoholic form of the preparation. The combination of Oralief® and the dissolved pharmaceutical preparation is then distilled at a temperature in the range of from 50° to lees than 100° C., preferably approximately at a temperature in the range of from about 70°–90° C., and more preferably at a temperature of approximately 75°–80° C. The distillation process, as noted above, is continued at a temperature within the specified range until all or almost all of the liquid volume equivalent to the volume of alcohol in solution has been removed.

An even further embodiment of the subject invention uses the process of converting an alcoholic/aqueous pharmaceutical preparation, having more then one type of alcohol, into a reduced alcoholic solution by distillation to remove the alcohol(s). Preferably the alcoholic/aqueous pharmaceutical preparation contains both ethanol and methanol and is distilled at a temperature in the range of from about 65° to less than 78.5° C., preferably approximately at a temperature in the range of from about 68°–75° C., and more preferably at a temperature of approximately 70°–72° C. The distillation process, as noted above, is continued at a temperature within the specified range until all or almost all of the liquid volume equivalent to the volume of methanol in solution has been removed. Furthermore, the typical levels of the ethanol and methanol combined used in the present invention range from about 2.5% to about 30% by volume, preferably at a range of from about 5% to about 25% by volume and more preferably from a range of approximately 10% to 20% by volume, based on the total composition volume before distillation, The alcohol removing distillation process of the present invention can be used on pharmaceutical compositions including but not limited to cosmetic products, such as skin care products, mouthwashes, toothpaste and tooth cleaning gels, and oral rinses marketed to maintain oral hygiene, control plaque, treat oral ulcers and sore throats.

Any surface active agent (surfactant) may be employed in the pharmaceutical formulation of the present invention. The preferred surface active agents are organic materials which aid in the dispersion of ingredients throughout the solution as well as dispersing the product throughout the oral cavity. Preferably, the surfactant used in the compositions of the present invention is a non-ionic surfactant or anionic surfactant. More preferably, the surfactant used in the composition of the present invention is the non-ionic surfactant, Pluronics F 127®, marketed by BASF Corp. Mount Olive, N.J. Pluronics F 127® is a block copolymer of propylene oxide and ethylene oxide, wherein the proplylene oxide block is sandwiched between two ethylene oxide blocks. The amount of surfactant employed is an amount sufficient to substantially solubilize the active ingredients in the formulation in water.

Furthermore, phenols may be added to the pharmaceutical formulation, at a range of from about 0.05% to about 2.5% by weight, preferably at a range of from about 0.1%–1.0% by weight.

Additionally, flavoring oils may be added to the pharmaceutical formulation. Suitable flavoring oils may be chosen from synthetic flavor oils, flavoring aromatics, oleo resins, and extracts derived from plants and the like, and combinations thereof. Illustrative examples of preferred flavoring oils include thymol, spearmint oil, cinnamon oil, oil of wintergreen (methyl salicylate), peppermint oil, clove oil, bay oil, eucalyptus oil, thyme oil, cedar lead oil, oil of nutmeg, oil of sage, oil of bitter almonds and the like. Such flavoring oils also include mints, such as peppermint, various fruit flavors, and cinnamon derivatives. Furthermore, the flavoring oils may comprise essential oils, natural or synthetic flavors or mixtures thereof including but not limited to oils derived from plants and fruits such as citrus oils, fruit essences, peppermint oils, spearmint oil, other mint oils, cloves oils, oil of wintergreen, anise, and the like. Moreover, other pharmaceutically active or cosmetic compositions such as aldehydes, esters can also be used in accordance with the invention.

The amount of flavoring oils employed in the formulation is normally dependent on a number of variables such as the flavor desired, the flavoring ingredient used, and the organoleptic strength desired. Accordingly, the amount may be varied within the capabilities of those skilled in the art. Typically, the flavoring oils are used in the formulation in amounts of from about 0.05% to about 2.0% by weight of the final composition.

For oral rinses and mouthwashes, the need to maintain effective antimicrobial effects is essential. In the present invention it was surprisingly and unexpectedly found that alcohol may be completely removed or reduced to lower levels without sacrificing anitmicrobial efficacy or clarity if the oral composition has been formulated in the presence of alcohol, and then removed by the process of distillation described in this invention.

EXAMPLE 1

In the following example an aqueous alcoholic mouthwash (Oralief® containing 14% ethanol by volume) was subjected to the process of distillation described in the present invention at a temperature range from about 75 to 80° C. The distillation process was continued at this temperature range until substantially all of the liquid volume equivalent to the ethanol was removed forming an aqueous based nonalcoholic preparation. The physical and chemical properties of the resulting aqueous based nonalcoholic preparation has been found by infra red (IR) analysis to have been stable both chemically and physically for at least 7 years. Furthermore, the original antimicrobial activity and other physical and therapeutic properties have been unchanged.

EXAMPLE 2

In the following example an aqueous alcoholic preparation was prepared and through the process of distillation of the present invention, the alcohols were A removed forming an aqueous based nonalcoholic cis-retinoic acid preparation. Cis-retinoic acid is an agent for acne and is usually supplied in an aqueous alcoholic preparation, and both alcohols, methanol and ethanol, are removed by distillation in the example. However, this invention is not limited to this example, but can be practiced in any equivalent fashion for any pharmaceutical ingredient without departing from the invention.

Cis-retinoic acid is usually used as a topical acne treatment which is supplied by drug manufacturers in an ointment or solution form containing methanol and other solubilizing substances as vehicles in the dissolution. One gram of a powdered form of cis-retinoic acid (CRA) was dissolved in 9 ml of methanol, and 1 ml of the resulting 10% methanol solution was slowly added to 100 ml of Oralief as a solubilizing vehicle. This produced a 1% solution of CRA in the vehicle. The bottle was capped and then shaken. The resulting aqueous alcoholic solution containing both methanol and ethanol was treated in accordance with the process of the present invention by distilling the mixture at approximately 80° C. until a volume equivalent to the alcohol had been removed. The resulting aqueous phase, after alcohol removal, appeared clear and similar to the vehicle without the pharmaceutical added.

The physical and chemical properties of the resulting substantially non-alcoholic, cis-retinoic acid product was measured by infra red (IR) analysis, and there resulted no change in I.R. graphic display even after one year. The I.R. graph also showed no peaks, for ethanol or methanol in the mixture. It appears that once the extremely water insoluble cis-retinoic acid was solubilized in an alcoholic aqueous vehicle the other ingredients in the vehicle continued to maintain the solubility in the remaining aqueous solution after removing the alcohol.

EXAMPLE 3

A cis-retinoic acid (CRA) solution is prepared by dissolving one gram of a powdered form of CRA in 9 ml of methanol resulting in a 10% CRA methanol solution. The CRA solution is next slowly added to 100 ml of a combination of Pluronic gel at a range of from about 0.005% to about 0.75% (gm/ml) with glycerin at a range of from about 1% to about 20%(ml/ 100 ml) and polyhydric alcohol sorbitol at a range of from about 2% to about 20% (ml/100 ml). The solution is then shaken. The resulting aqueous alcoholic solution containing both methanol and ethanol is treated in accordance with the process of the present invention by distilling the mixture at approximately 80° C., until a volume equivalent to the alcohol is removed. The resulting aqueous phase, after alcohol removal, appears clear and similar to the alcoholic product without the pharmaceutical added.

The invention has been described in considerable detail with reference to certain embodiments, and particularly with respect to the currently preferred embodiment thereof. However, it will be understood that variations, modifications and improvements may be made, particularly by those skilled in this art and in light of the teachings referred to herein within the spirit and scope of the invention as claimed.

What is claimed is:

1. A process for converting an alcohol containing aqueous pharmacologically active composition into a substantially non-alcoholic aqueous pharmacologically active composition comprising:
    (a) distilling the alcohol containing composition at a temperature in the range of from about 50° C. to less than 100° C.;

(b) removing in the distillation step an amount of alcohol from the said alcohol containing composition equivalent to approximately the volume of alcohol in the composition; and (c) recovering the substantially non-alcoholic aqueous composition remaining following steps (a) and (b).

2. A process according to claim 1, wherein the distillation of the alcohol containing composition is at a temperature within the range of from about 70° C. –90° C.

3. A process according to claim 1, wherein the distillation of the alcohol containing composition is at a temperature within the range of about 75° C. –80° C.

4. A process according to claim 1, wherein the alcohol is an alcohol having 1 to 3 carbon atoms.

5. A process according to claim 1, wherein the alcohol is an alcohol having 1 to 2 carbon atoms.

6. A process according to claim 1, wherein the alcohol is ethanol.

7. A process according to claim 6, wherein said ethanol is of a range from about 2.5%–30.0%.

8. A process according to claim 1, wherein the alcohol is methanol.

9. A process according to claim 1, wherein a flavoring oil is added.

10. A process according to claim 1, wherein said substantially non-alcoholic aqueous composition includes a pharmacological active oral hygiene agent and is useful as an oral hygiene composition.

11. A process according to claim 1, wherein phenol is added.

12. A process according to claim 11, wherein said phenol is of a range from about 0.10% to about 1.0% by weight.

13. A process according to claim 1, wherein a surfactant is added.

14. A process according claim 13, wherein said surfactant is of a range from about 0.005% to about 0.75% by weight.

15. A process according to claim 13, wherein said surfactant is a nonionic surfactant.

16. A process according to claim 13, wherein said surfactant is an anionic surfactant.

17. A process according to claim 1, wherein said alcohol containing aqueous pharmacologically active composition further comprises glycerin at a range of from about 1% to about 20% by volume.

18. A process according to claim 1, wherein said alcohol containing aqueous pharmacologically active composition comprises:

(a) a surfactant;

(b) glycerin; and (c) polyhydric alcohol sorbitol.

19. A process according to claim 18, wherein said surfactant is a nonionic surfactant.

20. A process according to claim 18, wherein said surfactant is Pluronic gel.

21. A process according to claim 20, wherein said Pluronic gel is of a range from about 0.005% to about 0.75% by weight.

22. A process according to claim 18, wherein the distillation of the alcohol containing composition is at a temperature within the range of from about 50° C. to less than 100° C.

23. A process according to claim 18, wherein the distillation of the alcohol containing composition is at a temperature within the range of from about 70° C. to 90° C.

24. A process according to claim 18, wherein the distillation of the alcohol containing composition is at a temperature within the range of about 75° C. –80° C.

25. A process according to claim 18, wherein said glycerin is of a range of about 1% to about 20% by volume.

26. A process according to claim 18, wherein said polyhydric alcohol sorbitol is of a range from about 2% to about 20% by volume.

27. A process for converting an alcohol containing aqueous pharmacologically active composition, having more than one alcohol, into a reduced alcoholic aqueous pharmacologically active composition comprising:

(a) distilling the alcohol containing composition at a temperature in the range of from about 65° C. to less than 78.5° C.;

(b) removing in the distillation step an amount of alcohol from the said alcohol containing composition equivalent to approximately the volume of at least one alcohol in the composition; and (c) recovering the reduced alcoholic aqueous composition remaining following steps (a) and (b).

28. A process according to claim 27, wherein the distillation of the alcohol containing composition is at a temperature within the range of from about 68° C.–75° C.

29. A process according to claim 27, wherein the distillation of the alcohol containing composition is at a temperature within the range of from about 70° C.–72° C.

30. A process according to claim 27, wherein the alcohol is a combination of ethanol and methanol.

31. A process according to claim 27, wherein a flavoring oil is added.

32. A process according to claim 27, wherein said reduced alcoholic aqueous composition includes a pharmacological active oral hygiene agent and is useful as an oral hygiene composition.

33. A process according to claim 27, wherein phenol is added.

34. A process according to claim 33, wherein said phenol is of a range from about 0.10% to about 1.0% by weight.

35. A process according to claim 27, wherein a surfactant is added.

36. A process according to claim 35, wherein said surfactant is of a range from about 0.00 5% to about 0.75% by weight.

37. A process according to claim 35, wherein said surfactant is a nonionic surfactant.

38. A process according to claim 35, wherein said surfactant is an anionic surfactant.

39. A process according to claim 27, wherein said alcohol containing aqueous pharmacologically active composition further comprises glycerin at a range of from about 1% to about 20% by volume.

\* \* \* \* \*

UNITED STATES PATENT AND TRADEMARK OFFICE
CERTIFICATE OF CORRECTION

PATENT NO. : 6,391,284 B1
DATED : May 21, 2002
INVENTOR(S) : Gangarosa, Sr.

It is certified that error appears in the above-identified patent and that said Letters Patent is hereby corrected as shown below:

Column 2,
Line 38, "Particular" should read -- Particularly --.
Line 63, "mature" should read -- mixture --.
Line 64, "disillusion" should read -- distillation --.

Column 3,
Line 4, following "was" delete the comma.
Line 33, after "75°" insert a hyphen.

Column 4,
Line 11, "OOralief®" should read -- Oralief® --.
Line 24, "lees" should read -- less --.
Line 33, "then" should read -- than --.
Line 50, after "distillation", delete the comma and in place thereof insert a period.

Column 5,
Line 67, after "were" delete "A".

Column 6,
Line 14, after "Oralief" insert a superscript ®.

Column 7,
Line 35, after "according" insert -- to --.

Column 8,
Line 50, "0.00 5%" should read -- 0.005% --.

Signed and Sealed this

Third Day of December, 2002

JAMES E. ROGAN
*Director of the United States Patent and Trademark Office*